(12) United States Patent
Newton

(10) Patent No.: US 8,709,010 B2
(45) Date of Patent: Apr. 29, 2014

(54) ELECTROSURGICAL SYSTEM

(75) Inventor: Michael David Newton, Newport (GB)

(73) Assignee: Gyrus Medical Limited, Cardiff (GB)

( * ) Notice: Subject to any disclaimer, the term of this patent is extended or adjusted under 35 U.S.C. 154(b) by 126 days.

(21) Appl. No.: 13/162,638

(22) Filed: Jun. 17, 2011

(65) Prior Publication Data

US 2011/0288542 A1 Nov. 24, 2011

Related U.S. Application Data

(63) Continuation of application No. 12/318,970, filed on Jan. 13, 2009, now Pat. No. 8,246,616, and a continuation-in-part of application No. 12/213,298, filed on Jun. 17, 2008, now abandoned.

(60) Provisional application No. 61/006,720, filed on Jan. 29, 2008.

(30) Foreign Application Priority Data

Jun. 19, 2007 (GB) .................................. 0711868.0
Jan. 16, 2008 (GB) .................................. 0800772.6

(51) Int. Cl.
*A61B 18/18* (2006.01)
*A61B 18/04* (2006.01)

(52) U.S. Cl.
USPC .................................. 606/42; 606/34; 606/37

(58) Field of Classification Search
None
See application file for complete search history.

(56) References Cited

U.S. PATENT DOCUMENTS 3,875,945 A 4/1975 Friedman
4,784,136 A 11/1988 Klein
(Continued)

FOREIGN PATENT DOCUMENTS

DE 3627221 2/1988
EP 1895924 3/2008
(Continued)

OTHER PUBLICATIONS

Search Report for GB0711868.0 (Date of Search: Oct. 31, 2007).
(Continued)

*Primary Examiner* — Aarti Bhatia Berdichevsky
*Assistant Examiner* — Weng Lee
(74) *Attorney, Agent, or Firm* — Nixon & Vanderhye PC

(57) ABSTRACT

An electrosurgical system includes an electrosurgical generator (1) including at least one source of radio frequency (RF) power, and a plurality of output connections (2, 3, 4), only one of the output connections at any one time being active in that it is able to receive radio frequency power from the source. The generator (1) includes selection means adapted to change the active output connection, and a controller adapted to control the supply of radio frequency power from the source to the active output connection. The system also includes a plurality of electrosurgical assemblies, each including an electrosurgical instrument (5, 6, 7) and a cable (8, 9, 10) connecting the electrosurgical instrument to one of the output connections (2, 3, 4). The electrosurgical instruments (5, 6, 7) each include a handswitch (17, 18, 19) adapted to send a signal to the generator (1) to change the active output connection. The selection means is such that a signal sent from the handswitch (17, 18, 19) of the active instrument (5, 6, 7) can cause the generator (1) to change the active output connection to a different output connection (2, 3, 4), but a signal sent from the handswitch of an instrument other than the active instrument does not immediately cause the selection means to change the active output connection to a different output connection.

10 Claims, 3 Drawing Sheets

(56) References Cited

U.S. PATENT DOCUMENTS

| | | | |
|---|---|---|---|
| 4,800,878 | A | 1/1989 | Cartmell |
| 4,834,095 | A | 5/1989 | Miller |
| 5,342,356 | A | 8/1994 | Ellman et al. |
| 5,817,091 | A | 10/1998 | Nardella et al. |
| 5,951,545 | A | 9/1999 | Schilling et al. |
| 6,287,304 | B1 | 9/2001 | Eggers et al. |
| 6,312,428 | B1 | 11/2001 | Eggers et al. |
| 6,508,809 | B1 | 1/2003 | Bacher |
| 6,666,860 | B1 * | 12/2003 | Takahashi ............... 606/34 |
| 6,676,660 | B2 | 1/2004 | Wampler et al. |
| 6,679,875 | B2 * | 1/2004 | Honda et al. ............ 606/1 |
| 7,353,068 | B2 * | 4/2008 | Tanaka et al. ........... 700/17 |
| 7,543,588 | B2 * | 6/2009 | Wang et al. ............. 128/898 |
| 2004/0019347 | A1 | 1/2004 | Sakurai et al. |
| 2004/0097916 | A1 | 5/2004 | Thompson et al. |
| 2004/0215131 | A1 | 10/2004 | Sakurai |
| 2005/0043828 | A1 | 2/2005 | Tanaka et al. |
| 2005/0143724 | A1 | 6/2005 | El-Galley et al. |
| 2006/0217700 | A1 | 9/2006 | Garito et al. |
| 2007/0049927 | A1 | 3/2007 | Saltzman |
| 2008/0241575 | A1 | 10/2008 | Lavoie et al. |

FOREIGN PATENT DOCUMENTS

| | | |
|---|---|---|
| GB | 816720 | 7/1959 |
| GB | 2206796 | 5/1988 |
| GB | 2450679 | 1/2009 |
| GB | 2456353 | 7/2009 |
| WO | WO 99/01074 | 1/1999 |
| WO | WO 01/37745 A1 | 5/2001 |
| WO | WO 2004/045436 | 6/2004 |
| WO | WO 2006/125558 | 11/2006 |

OTHER PUBLICATIONS

Search Report for GB1018344.0 (Date of Search: Nov. 25, 2010).
Search Report for GB0800772.6 (Date of Search: May 16, 2008).
International Search Report issued in corresponding International Application No. PCT/GB2009/000008, mailed Apr. 6, 2009.
Third Notification of Office Action, Third Office Action and Search Report issued Aug. 15, 2013 in Chinese Application No. 201010578916.7.
English Translations of Third Notification of Office Action, Third Office Action and Search Report issued Aug. 15, 2013 in Chinese Application No. 201010578916.7.
Office Action issued Jul. 2, 2013 in Mexican Application No. MX/a/2010/007857.

* cited by examiner

ELECTROSURGICAL SYSTEM

This application is a continuation of U.S. patent application Ser. No. 12/318,970, filed 13 Jan. 2009 now U.S. Pat. No. 8,246,616, and a Continuation in Part of U.S. patent application Ser. No. 12/213,298, filed 17 Jun. 2008 now abandoned, and claims the benefit of U.S. Provisional Patent Application No. 61/006,720, filed 29 Jan. 2008, and claims priority to United Kingdom Application No. 0800772.6, filed 16 Jan. 2008 and United Kingdom Application No. 0711868.0, filed 19 Jun. 2007, the entire contents of all being incorporated herein by reference This invention relates to an electrosurgical system including an electrosurgical generator, and a plurality of electrosurgical instruments for use therewith.

The majority of electrosurgical generators are designed to have only one instrument attached to the generator at any one time. However, there is an increasing trend, with ever more sophisticated electrosurgery systems, to have multiple instruments connected to the generator at any one time. U.S. Pat. Nos. 5,342,356 and 6,508,809 relate to two examples of electrosurgical systems in which multiple instruments can be connected to a single generator. These patent specifications describe how shaped-connectors, colour-coding and distinct symbols can be used to assist with the connection of these multiple instruments, and to ensure that the correct instrument is connected to the appropriate output of the generator.

Another example of an electrosurgery system with multiple instruments connected to a single generator is described in US patent application 2004/0215131. Like most of these known electrosurgical generators, this application describes a system that only allows for the operation of one of the attached instruments at any one time. Handswitches are present on the electrosurgical instruments, and the pressing of any of the handswitches immediately makes that instrument the "active" instrument.

It is an aim of the present invention to provide an improved electrosurgical system in which various electrosurgical instruments can be selected.

One aspect of the present invention provides an electrosurgical system including;
  i) an electrosurgical generator, the electrosurgical generator including;
    a) at least one source of radio frequency (RF) power,
    b) a plurality of output connections, only one of the output connections at any one time being active in that it is able to receive radio frequency power from the source,
    c) selection means adapted to change the active output connection, and
    d) a controller adapted to control the supply of radio frequency power from the source to the active output connection;
  ii) a plurality of electrosurgical assemblies, each including an electrosurgical instrument and a cable connecting the electrosurgical instrument to one of the output connections, a first electrosurgical assembly being connected to a first output connection of the generator, and a second electrosurgical assembly being connected to a second output connection of the generator, the electrosurgical instrument being connected to the active output connection being designated the active instrument, at least one of the first and second electrosurgical assemblies including a handswitch assembly adapted to cause at least three different actions to occur,
    a first type of activation of the handswitch assembly causing the controller to supply radio frequency power to the electrosurgical assembly in a first mode of operation, a second type of activation of the handswitch assembly causing a tissue cutting action, and a third type of activation of the handswitch assembly causing the selection means to change the active output connection to a different output connection.

In one arrangement the first mode of operation is such that the generator supplies a coagulating RF signal to the electrosurgical assembly. A second type of activation of the handswitch may then cause the controller to supply radio frequency power to the electrosurgical assembly in a second mode of operation. The second mode of operation may be such that the generator supplies a cutting RF signal to the electrosurgical assembly. However, in one arrangement the second type of activation of the handswitch assembly activates a mechanical cutting blade.

In one arrangement the handswitch assembly comprises a single button capable of being manipulated in at least three different directions. However, in another arrangement the handswitch assembly comprises at least three different buttons, each capable of being manipulated independently. In a further arrangement the handswitch assembly comprises at least two different buttons, a first button of said two buttons capable of being manipulated to select between the first and third types of activation of said handswitch assembly, and a second button arranged to select the second type of activation of said handswitch assembly.

In one arrangement both of the first and second electrosurgical assemblies includes a handswitch assembly adapted to cause at least three different actions to occur.

In one arrangement the third type of activation of the handswitch assembly of an electrosurgical assembly causes the selection means to change the active output connection to the output connection associated with that electrosurgical assembly. Alternatively, in another arrangement the third type of activation of the handswitch assembly of an electrosurgical assembly causes the selection means to change the active output connection to the output connection associated with one of the other electrosurgical assemblies.

In one arrangement the electrosurgical instruments contain at least one lamp, capable of being illuminated to indicate which electrosurgical instrument is the active instrument. In such an arrangement at least part of the handswitch assembly may be translucent and the at least one lamp is capable of illuminating that part of the handswitch assembly.

The present specification also describes an electrosurgical system comprising:
  i) an electrosurgical generator comprising:
    a) at least one source of radio frequency (RF) power,
    b) a plurality of output connections, only one of the output connections at any one time being active in that it is able to receive radio frequency power from the source, and
    c) means for controlling the supply of radio frequency power from the source to the active output connection; and
  ii) a plurality of electrosurgical assemblies, each including a respective electrosurgical instrument and a cable connecting that electrosurgical instrument to one of the output connections, each electrosurgical instrument being connected to a respective output connection of the generator, the electrosurgical instrument connected to the active output connection being designated the active instrument, each of the electrosurgical instruments including a handswitch adapted to change the active output connection;
  the system being such that a signal sent from the handswitch of the active instrument changes the active output connection to a different output connection, but a signal sent from the handswitch of an instrument other than the active instrument does not change the active output connection to a different output connection.

For the purposes of this specification, the instrument to which electrosurgical power can be supplied is described as the "active" instrument, and that instrument is said to be in "focus". The problem with systems such as the one described in US patent application 2004/0215131 is that the transfer of focus from one instrument to another can be effected regardless of whether the instrument previously in focus has finished its work. There is, therefore, the possibility one surgeon can take control of the active output of the electrosurgical generator, before the other surgeon would like this to occur. It is frequently the case that a more experienced surgeon will work alongside a less experienced surgeon, either for training purposes or because one surgeon is pre-eminent in his or her field. It is, therefore, advantageous to give the more experienced surgeon control over the transfer of the active instrument, as opposed to the less experienced surgeon. The present arrangement ensures that, when this safety mode is activated, a signal sent from a non-active instrument does not immediately cause the selection means to change the active output connection.

In a preferred arrangement, the system is such that the active output connection is transferred from one output connection to another output connection on receipt of a sequence of signals from the handswitches of the electrosurgical instruments. In one arrangement, the system is such that the sequence of signals comprises a first signal from the handswitch of the active instrument, followed by a second signal from the handswitch of an instrument other than the active instrument, thereby causing the active output connection to be transferred to the instrument sending the second signal. In this way, the transfer of focus can only proceed after consent to the transfer has effectively been given from the instrument currently in focus.

Alternatively, the system is such that the sequence of signals comprises a first signal from the handswitch of an instrument other than the active instrument, followed by a second signal from the handswitch of the active instrument, thereby causing the active output connection to be transferred to the instrument sending the first signal. In this alternative protocol, consent for the transfer of focus is requested from an instrument other than the one currently in focus, and this consent is effectively given by the user of the instrument in focus prior to any transfer taking place. Whichever protocol is employed, the change in the active instrument only goes ahead when there is a positive signal from both the instrument requesting the focus, and, unlike in US 2004/0215131, also from the instrument currently in focus.

In one convenient arrangement, the handswitch of one or more of the electrosurgical instruments comprises a switch having at least first, second and third positions. Moving the switch to the first position causes the generator to supply a cutting radio frequency signal to the active output connection, while moving the switch to the second position causes the generator to supply a coagulating radio frequency signal to the active output connection. Moving the switch to the third position sends a signal to the generator, to request or give permission for the transfer of the active output to or from that instrument.

Alternatively, the handswitch of one or more of the electrosurgical instruments comprises a switch assembly comprising at least first, second and third buttons. Depressing the first button causes the generator to supply a cutting radio frequency signal to the active output connection, while depressing the second button causes the generator to supply a coagulating radio frequency signal to the active output connection. Depressing the third button sends a signal to the generator, once again to request or give permission for the transfer of the active output to or from that instrument.

The electrosurgical systems described above effectively "push" the active focus from the currently active instrument to an alternative instrument not currently in focus. The system of US 2004/0215131 effectively "pulls" the active focus from the currently active instrument to an alternative instrument not currently in focus. It is conceivable that the users of the electrosurgical system may wish to have the option to set up the operating environment with either of these arrangements, depending on the circumstances. The electrosurgical system according to the present invention can, therefore, be set to an alternative mode in which a signal sent from the handswitch of an instrument other than the active instrument does immediately change the active output connection to a different output connection.

The present specification also describes an electrosurgical system comprising:
  i) an electrosurgical generator comprising:
    a) at least one source of radio frequency (RF) power,
    b) a plurality of output connections, only one of the output connections at any one time being active in that it is able to receive radio frequency power from the source,
    c) hierarchy means adapted to appoint at least one of the output connections as a primary output connection, and at least one other output connection as a secondary output connection,
    d) means for controlling the supply of radio frequency power from the source to the active output connection, and
  ii) a plurality of electrosurgical assemblies, each including a respective electrosurgical instrument and a cable connecting that electrosurgical instrument to one of the output connections, each electrosurgical instrument being connected to a respective output connection of the generator, the electrosurgical instrument connected to the active output connection being designated the active instrument, an electrosurgical instrument connected to a primary output connection being designated a primary instrument, and an electrosurgical instrument connected to a secondary output connection being designated a secondary instrument, each of the electrosurgical instruments including a handswitch adapted to send a signal to the selection means to change the active output connection,
  the system being such that a signal sent from the handswitch of a primary instrument changes the active output connection to a different output connection, but a signal sent from the handswitch of a secondary instrument does not immediately change the active output connection to a different output connection.

This arrangement is a variation on the "push" or "pull" modes described above, in which the ability to switch the focus of the instruments depends on the hierarchy of the instruments concerned. A primary instrument, typically designated for a more experienced surgeon, can "pull" the focus from other secondary instruments without requiring further authorisation or warning. However, other secondary instruments, typically designated for less experienced surgeons or less vital types of electrosurgical instrument, can not "pull" the focus from a primary instrument without the primary instrument giving permission for said transfer, or "pushing" the focus voluntarily to the secondary instrument.

Typically, the hierarchy means is capable of receiving signals so as to change the or each primary output connection. In this way, the setup of the electrosurgical system, including which instruments are designated as primary or secondary instruments, can be flexibly changed to suit individual circumstances.

The electrosurgical system described above can conveniently be used in conjunction with indication means, as described in our co-pending application GB 0711868.0, for giving a visible indication of which instrument is in focus.

The invention will now be described in more detail, by way of example only, with reference to the drawings, in which.

Figure 1:
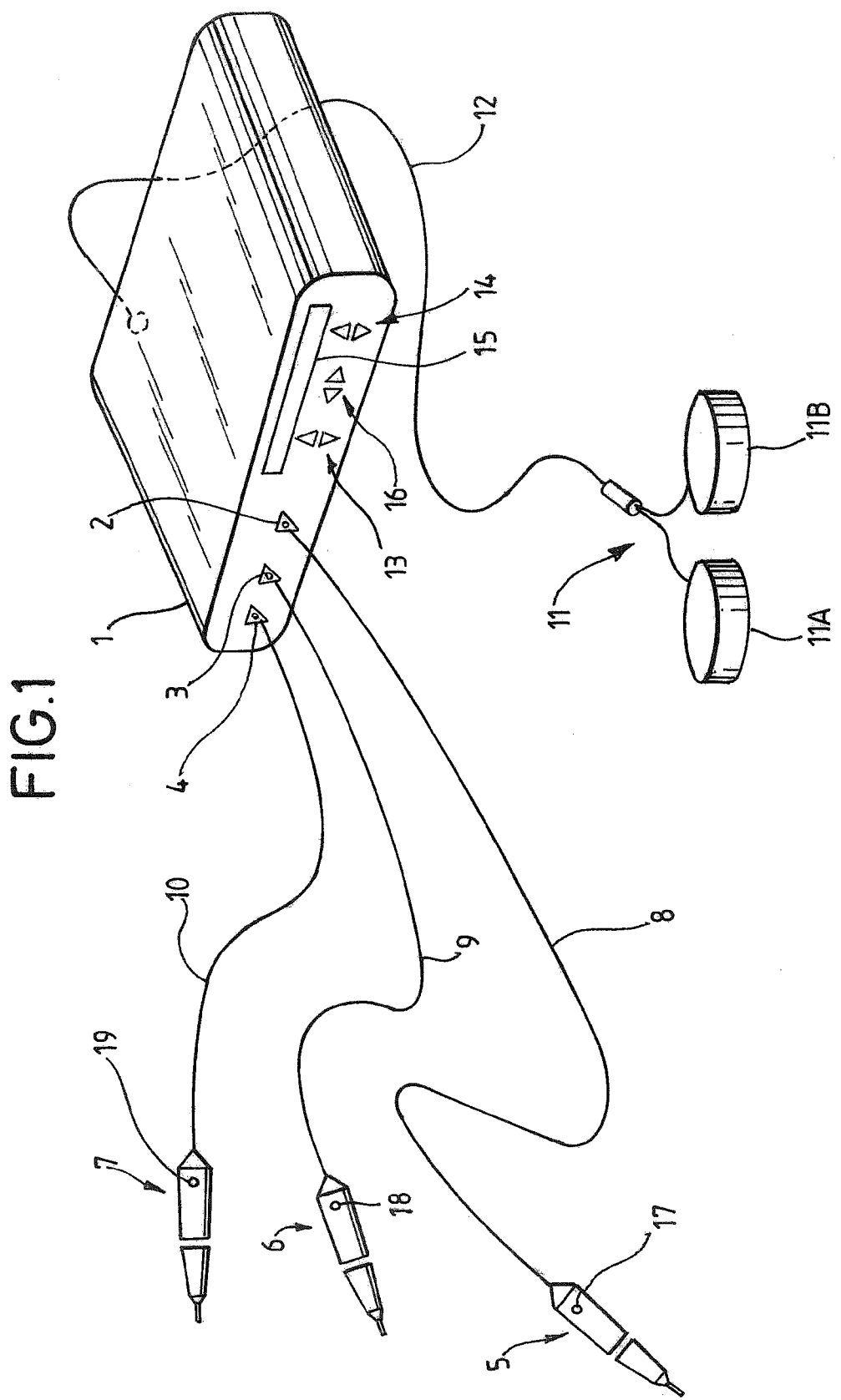
FIG. 1 is a schematic view of an electrosurgical system constructed in accordance with the invention.

Referring to FIG. 1, a generator 1 has a output sockets (connections) 2, 3, 4, providing a radio frequency (RF) output for instruments 5, 6, 7, via connection cords 8, 9, 10. Activation of the generator 1 may be performed from the instruments 5, 6, 7, via handswitches 17, 18, 19, or by means of a footswitch unit 11, as shown, connected to the rear of the generator by a footswitch connection cord 12. In the illustrated embodiment, the footswitch unit 11 has two footswitches 11A and 11B for selecting a coagulation mode and a cutting mode of the generator 1 respectively. The generator front panel has push buttons 13 and 14 for respectively setting coagulation and cutting power levels, which are indicated in a display 15. Push buttons 16 are provided as an additional means for selection between the instruments 5, 6, and 7.

Figure 2:
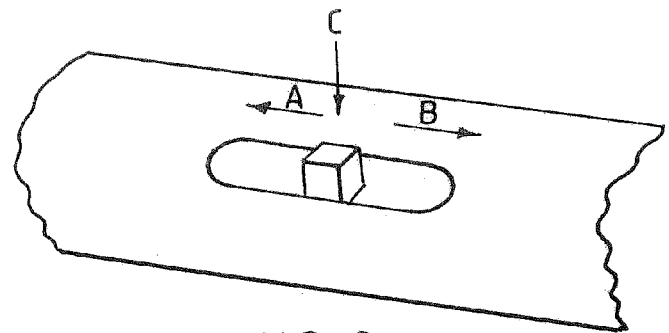
FIG. 2 is a schematic perspective view of a part of an electrosurgical instrument forming part of the system of FIG. 1.

FIG. 2 shows a typical handswitch 17 mounted on an instrument 5. The switch 17 is movable in a first direction A to send a signal to the generator 1 such that a cutting RF signal is sent to the instrument 5. Alternatively, the switch is movable in the opposite direction B to send a signal to the generator 1 such that a coagulating RF signal is sent to the instrument 5. There may additionally be other positions (not shown) into which the switch is movable, in order to obtain further variations (such as blended cut and coagulation signals etc.). However, the switch 17 may also be moved downwardly in a direction C in order to send a signal to the generator 1 to change the instrument to which the generator sends the RF signals, as will be further described below.

In use, the user selects from a menu of options whether the generator 1 is to operate in a "Push" or "Pull" mode when selecting between the instruments 5, 6 and 7. Supposing that the operator has selected the "Push" mode, one instrument 5 will be defaulted to become the initial active instrument. Thus, when the footswitch unit 11 or the handswitch 17 is activated, RF signals will be sent to the instrument 5, but not to the instruments 6 or 7. A lamp (not shown) may be illuminated on the instrument 5 to show that it has been selected as the active instrument.

If a user of the system wishes to use either of the instruments 6 and 7, one of them must be arranged to become the active instrument. As the generator 1 has been set to the "Push" mode, to do this a user must first depress the handswitch 17 on the instrument 5, to indicate that consent is given to the focus being diverted away from the instrument 5. After this signal from the instrument 5 has been received by the generator 1, if the handswitch 18 is depressed on the instrument 6, then the focus will be diverted to the instrument 6, and this instrument will become the active instrument and be ready for use. In this way, the instrument 6 does not become usable until the user of the instrument 5 has consented to the transfer. If the user of the instrument 6 depresses the handswitch 18 before the consent signal has been given from the instrument 5, the generator 1 will take no action and the focus will not be transferred.

This arrangement ensures that the user of the instrument 5 is not surprised by the transfer of focus away from the instrument 5 before the user is ready and prepared for this to occur. In a similar fashion, once the focus has been transferred to the instrument 6, the generator 1 will not transfer the focus to another instrument if a consent signal from the instrument 6 has not been received. To transfer the focus back to the instrument 5, the handswitch 18 on the instrument 6 is depressed (to provide a consent signal to the generator 1), followed by depression of the handswitch 17 on the instrument 5. A similar procedure is followed to transfer the focus to the instrument 7.

In an additional or alternative arrangement, if the active instrument is the instrument 5, and the handswitch 18 is depressed on the instrument 6 before a consent signal has been given from the instrument 5, the generator 1 sends a signal to request permission for the transfer. This may be in the form of a message displayed on the display 15, an audible tone emitted by the generator 1, or by causing a lamp (not shown) to flash on the instrument 5. If the user of the instrument 5 consents to the transfer of focus, the user depresses the handswitch 17 to send a signal to the generator 1, which then transfers the focus to make the instrument 6 the active instrument. In this way, permission can be given for the change of instrument focus, after a request from the new instrument, rather than before such a request is made.

Another way in which the generator 1 can be set up is to transfer the instrument focus in a "Pull" mode. In this way, if the handswitch 18 is depressed on the instrument 6 before a consent signal has been given from the instrument 5, the generator 1 sends a signal to transfer the instrument focus regardless of whether or not there has been a consent to the transfer from the currently active instrument. A further option is for different instruments to be given greater status than others. For example, the instrument 5 may be designated for the most senior surgeon attending the procedure, and this may be given full rights. In this way, the instrument 5 may be able to "Pull" the focus from the other instruments 6 and 7, without requiring consent to such a transfer. Furthermore, the other instruments 6 and 7 may not have equivalent rights, requiring the senior instrument 5 to "Push" the focus to them by giving consent as previously described. This arrangement is suitable for a situation in which the instrument 5 is used by an experienced senior surgeon, and the instruments 6 and 7 by less senior or less experienced colleagues.

Figure 3:
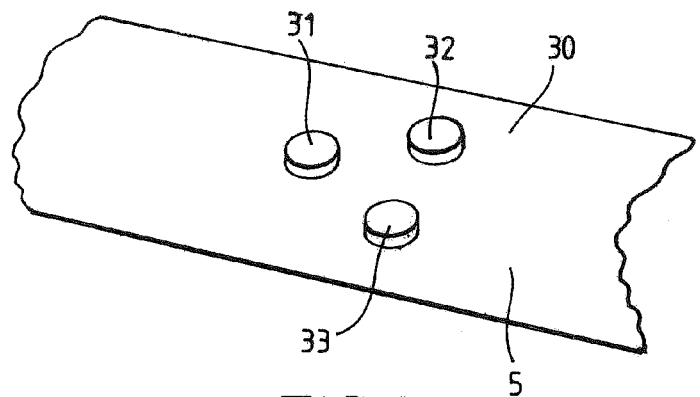
FIG. 3 is a schematic perspective view of a part of an alternative electrosurgical instrument forming part of the system of FIG. 1.

FIG. 2 shows an arrangement in which a single handswitch 17, 18 or 19 is used on each instrument 5, 6 or 7, each handswitch having multiple positions. FIG. 3 shows an alternative arrangement in which each handswitch assembly 30 comprises three handswitch buttons 31, 32 and 33 respectively. The button 31 can be used to send a signal to the generator 1 such that a cutting RF signal is sent to the instrument 5, 6 or 7. The button 32 is used to send a signal to the generator 1 such that a coagulating RF signal is sent to the instrument 5, 6 or 7. Finally, the button 33 is used to send a signal to the generator 1 to change the instrument to which the generator sends the RF signals, as previously described. An advantage of this arrangement is that the buttons 31 and 32 are isolated when the associated instrument 5, 6 or 7 is not in focus, and the operation of the buttons when the instrument 5, 6 or 7 is not in focus will not result in any RF signals being provided to the instrument. It is only when the focus has been deliberately shifted to the instrument that the operation of the buttons 31 or 32 will result in an RF signal being provided to the instrument. Inadvertent operation of the instrument is, therefore, prevented.

Figure 4:
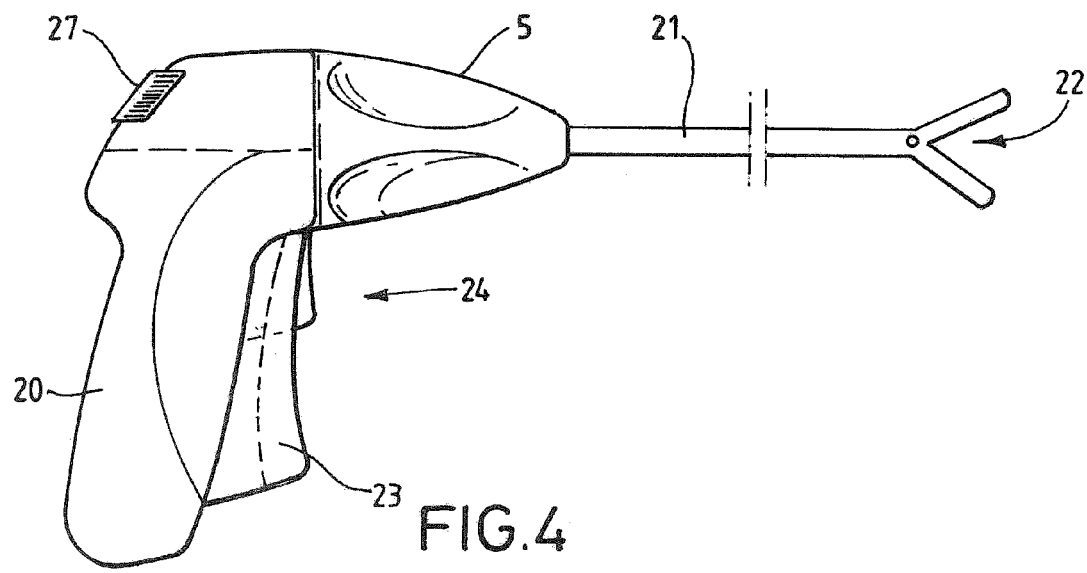
FIG. 4 is side view of an electrosurgical instrument forming part of the system of FIG. 1.

FIG. 4 shows an example of an instrument 5, such as a forceps instrument including a handpiece 20, a shaft 21 and a jawed end-effector 22 at the distal end of the shaft. An actuating handle 23 opens and closes the jaws 22, while a button 24 activates a cutting mechanism (not shown), which may either be the movement of a mechanical blade or the sending of a cutting signal to an electrosurgical cutting element. When actuation of the handle 23 has closed the jaws 22, activation of the button 24 causes the generator 1 to send a coagulating RF signal to the end-effector 22. Activation of a further handswitch 27 causes the generator 1 to send a cutting RF signal to the end-effector 22. Both the handswitches 24 and 27 are translucent and each has a lamp therein, so that when the instrument 5 is selected as the active instrument, the handswitches 24 and 27 are illuminated. Either the lamps or the translucent handswitch casings are coloured, such that the coagulation handswitch 24 is illuminated with, for example, a blue colour, while the cutting handswitch 27 is illuminated with for example, a yellow colour.

The handswitch 27 also has a further position (a lateral movement as opposed to depressing the switch, or vice versa) that sends a signal to the generator 1 to request or consent to the transfer of focus to another instrument, or request that the focus is moved from another instrument to that instrument.

Figure 5:
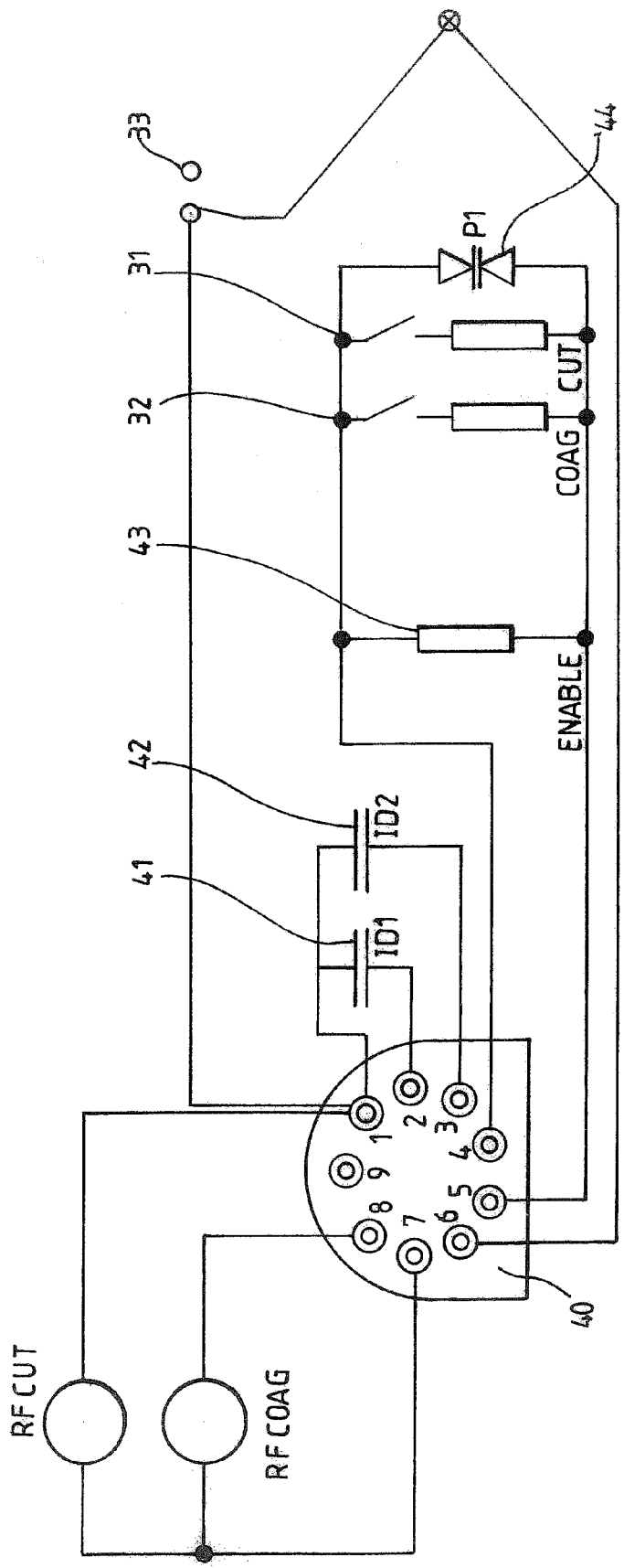
FIG. 5 is a schematic view of a circuit diagram showing the operation of the system of FIG. 1.

FIG. 5 shows a circuit diagram illustrating how the signal to request a transfer of the focus is generated. A connector 40 is shown attached to the generator 1, and includes nine pins 1 to 9. The pin 1 is an RF reference pin, completing a circuit from the pin 6, as will be described in due course. The pins 2 and 3 are connected to capacitors 41 and 42, used to identify the instrument 5 to the generator 1. The pins 4 and 5 form a circuit in which the handswitch buttons 31 and 32 are present, for coagulation and cutting respectively. Also included within this circuit are an enabling resistor 43 and a rectifier 44. The pin 6 forms, with the pin 1, a thermocouple circuit for measuring the temperature of the tip of the instrument 5, and also the button 33, for indicating or confirming a request for the transfer of the active instrument. A cutting electrode (not shown) is connected between the pin 1 and the pin 7, while a coagulating electrode (not shown) is connected to between the pin 7 and the pin 8. The pin 9 is spare.

The circuit of FIG. 5 has the advantage that, unlike the other pins, there is a current applied between the pins 6 and 1, regardless of whether the instrument 5 is currently in focus. Thus, when the switch 33 is depressed, interrupting the circuit between the pins 6 and 1, a signal can be detected by the generator 1 regardless of whether or not the instrument 5 is currently active. In this way, a signal from any of the instruments 5, 6 or 7 can be detected by the generator 1, even if only one of the instruments is in focus (or indeed even if none of the instruments is in focus). This is essential if the transfer of the focus is to be requested by a signal sent from an instrument not currently in focus. Other circuit arrangements are of course possible, but care must be taken to ensure that signals can be sent by (or detected from) instruments other that the one currently in focus. If this is not the case, it would be difficult to ensure that the transfer of focus can be effected by handswitching, as opposed to the buttons 16 present on the fascia of the generator 1.

The generator 1 includes circuitry (software plus switching relays) constituting selection means for changing which of the output connections 2, 3, 4 becomes "live". The generator 1 also includes circuitry (or possibly software control) constituting a controller for controlling the on/off supply of the RF signals to the live output connections. Finally, the generator 1 is software controlled to act as hierarchy means for determining which of the output connections 2, 3, 4 takes precedence.

The invention claimed is:

1. An electrosurgical system including;
   i) an electrosurgical generator, the electrosurgical generator including;
      a) at least one source of radio frequency (RF) power,
      b) a plurality of output connections, only one of the output connections at any one time being active in that it is able to receive radio frequency power from the source,
      c) selection means adapted to change the active output connection, and
      d) a controller adapted to control the supply of radio frequency power from the source to the active output connection;
   ii) a plurality of electrosurgical assemblies, each including an electrosurgical instrument and a cable connecting the electrosurgical instrument to one of the output connections, a first electrosurgical assembly being connected to a first output connection of the generator, and a second electrosurgical assembly being connected to a second output connection of the generator, the electrosurgical instrument being connected to the active output connection being designated the active instrument, at least one of the first and second electrosurgical assemblies including a handswitch assembly located on the electrosurgical instrument, the handswitch assembly comprising at least three different buttons, each of the at least three different buttons being capable of being manipulated independently and being adapted to cause at least three different actions to occur,
   an activation of a first button causing the controller to supply radio frequency power to the electrosurgical assembly in a first mode of operation, an activation of a second button causing a tissue cutting action, and an activation of a third button causing the selection means to change the active output connection to a different output connection.

2. The electrosurgical system according to claim 1, wherein the first mode of operation is such that the generator supplies a coagulating RF signal to the electrosurgical assembly.

3. The electrosurgical system according to claim 1, wherein an activation of the second button causes the controller to supply radio frequency power to the electrosurgical assembly in a second mode of operation to effect the tissue cutting action.

4. The electrosurgical system according to claim 3, wherein the second mode of operation is such that the generator supplies a cutting RF signal to the electrosurgical assembly.

5. The electrosurgical system according to claim 1, wherein the activation of the second button activates a mechanical cutting blade.

6. The electrosurgical system according to claim 1, wherein both of the first and second electrosurgical assemblies includes a handswitch assembly located on each respective electrosurgical instrument and adapted to cause at least three different actions to occur.

7. The electrosurgical system according to claim 1, wherein the activation of the third button of an electrosurgical assembly causes the selection means to change the active output connection to the output connection associated with that electrosurgical assembly.

8. The electrosurgical system according to claim 1, wherein the activation of the third button of an electrosurgical assembly causes the selection means to change the active output connection to the output connection associated with one of the other electrosurgical assemblies.

9. The electrosurgical system according to claim 1, wherein the electrosurgical instruments contain at least one lamp, capable of being illuminated to indicate which electrosurgical instrument is the active instrument.

10. The electrosurgical system according to claim 9, wherein at least part of the handswitch assembly is translucent and the at least one lamp is capable of illuminating that part of the handswitch assembly.

* * * * *